United States Patent [19]

Robson et al.

[11] Patent Number: 4,853,414

[45] Date of Patent: Aug. 1, 1989

[54] HALOGENATED ESTERS

[75] Inventors: Michael J. Robson; John Williams, both of Bracknell, United Kingdom

[73] Assignee: Imperial Chemical Industries PLC, London, England

[21] Appl. No.: 114,732

[22] Filed: Oct. 30, 1987

[30] Foreign Application Priority Data

Nov. 6, 1986 [GB] United Kingdom ............... 8626520

[51] Int. Cl.⁴ .................... C07C 69/74; A01N 53/00
[52] U.S. Cl. .................. 514/531; 560/124; 568/715; 568/812; 568/813; 568/807; 568/626; 568/630; 568/631; 568/645; 568/647; 570/127; 570/128; 562/423; 549/223
[58] Field of Search .............. 560/124; 514/531; 568/715, 812, 813, 807, 626, 630, 631, 645, 647; 570/127, 128; 562/423; 549/223

[56] References Cited

U.S. PATENT DOCUMENTS

| | | | |
|---|---|---|---|
| 4,183,950 | 1/1980 | Naumann et al. | 514/531 |
| 4,252,820 | 2/1981 | Lantzsch | 514/531 |
| 4,370,346 | 1/1983 | Punja | 560/124 |
| 4,405,640 | 9/1983 | Punja | 560/124 |
| 4,423,066 | 12/1983 | Fuchs et al. | 514/531 |
| 4,551,546 | 11/1985 | Punja | 560/124 |
| 4,567,199 | 1/1986 | Crowley | 514/531 |
| 4,714,790 | 12/1987 | Bushell | 560/124 |

Primary Examiner—Paul Lieberman
Assistant Examiner—Helene Kirschner
Attorney, Agent, or Firm—Cushman, Darby & Cushman

[57] ABSTRACT

Compounds of formula (I), useful as insecticides and knockdown agents:

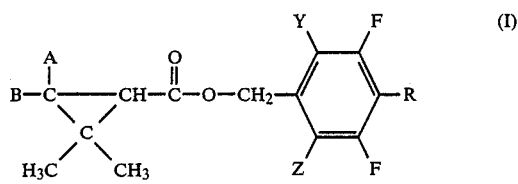

where Y is $C_{1-6}$ alkoxy, Z is halo or $C_{1-6}$ alkoxy; R is $-(CH_2)_p-(O)_m-R^3$ where m and p may be 0 or 1; $R^3$ is $C_{1-6}$ alkyl, phenyl or benzyl, or when m is 0, $R^3$ is $C_{1-6}$ alkenyl, haloalkenyl, alkynyl or haloalkynyl, and either (a) A and B are both $C_{1-4}$ alkyl or (b) A is hydrogen and B is $(R^1)(R^2)C=CH-$ where $R^1$ and $R^2$ are selected from methyl, chloro, bromo, fluoro and trifluoromethyl.

14 Claims, No Drawings

HALOGENATED ESTERS

This invention relates to novel cyclopropane derivatives useful as insecticides, to processes for their preparation, to compositions comprising them and to methods of combating insect and similar invertebrate pests using them.

Certain naturally occurring esters of cyclopropane carboxylic acids have long been known to possess insecticidal properties, but these compounds have been too easily degraded by ultra violet light to be of much use in agriculture. Several groups of synthetic compounds based on cyclopropane carboxylic acids (for example those disclosed in British patent specifications Nos. 1,243,858 and 1,413,491) have been evaluated in an attempt to discover compounds of sufficient light stability for use as general agricultural insecticides.

A particularly useful group of such compounds is that disclosed in British patent specification No. 2,000,764 and U.S. Pat. No. 4,183,948. These compounds combine good light stability with excellent contact and residual insecticidal properties, but, in common with the compounds described in British patent specifications Nos. 1,243,858 and 1,413,491, they possess little or no fumigant activity. A further group of compounds, halobenzyl esters of 3-(2,2-dihalovinyl)-2,2-dimethylcyclopropane carboxylic acids, is described in U.S. Pat. No. 4,183,950 as having insecticidal properties but there is no indication that the compounds possess fumigant activity.

The present invention relates to certain novel halogenated benzyl esters of substituted cyclopropanecarboxylic acids with a high level of insecticidal and acaricidal activity which may be used not only as contact or residual insecticides and acaricides, but also as fumigant insecticides and acaricides. In addition to their toxic effect, the compounds according to the invention also exhibit a high level of knockdown activity against certain insect pest species.

In a first aspect the invention provides compounds of formula (I):

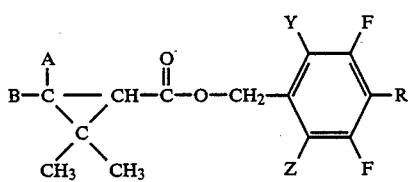
(I)

wherein Y represents alkoxy of up to six carbon atoms; Z represents halo or alkoxy of up to six carbon atoms; R represents a group of formula:

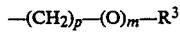

—(CH$_2$)$_p$—(O)$_m$—R$^3$ wherein each of m and p may have a value selected from zero and one, R$^3$ represents alkyl containing up to six carbon atoms, phenyl or benzyl, and additionally R$^3$ may represent hydrogen when both m and p have the value zero, or R$^3$ may represent alkenyl containing up to six carbon atoms, haloalkenyl containing up to six carbon atoms, alkynyl containing up to six carbon atoms or haloalkynyl containing up to six carbon atoms when m has the value zero; and either (a) A and B are both selected from alkyl containing up to four carbon atoms, or (b) A represents hydrogen and B represents a group of formula:

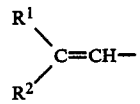

wherein R$^1$ and R$^2$ are each selected from methyl, fluoro, chloro, bromo and trifluoromethyl.

Preferred compounds according to the invention are those wherein R represents alkyl of up to four carbon atoms, alkoxy of up to four carbon atoms, alkenyl of up to four carbon atoms, alkynyl of up to four carbon atoms and alkoxymethyl of up to four carbon atoms in the alkoxy moiety.

Particularly preferred compounds according to the invention are those wherein Y represents methoxy, Z represents fluoro, R is selected from hydrogen, methyl, methoxymethyl, allyl and propargyl, A represents hydrogen and B represents a group of formula:

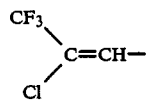

It will be appreciated by those skilled in the art that the compounds represented by formula (I) are capable of existing in various geometrical and stereoisomeric forms. Thus there may be cis and trans isomers arising from the substitution pattern of the cyclopropane ring, and E- and Z-isomers arising from the substituted vinyl group when R$^1$ is not identical with R$^2$. In addition each asymmetrically substituted carbon atom of the cyclopropane ring is capable of existing in either of two stereoisomeric forms, the R-form and the S-form.

Within the group of compounds represented by Formula (I) the cis isomers usually have better insecticidal properties than the trans isomers or the mixture of cis and trans isomers; the (+)-cis isomers being particularly preferred.

A particularly useful single isomer of a compound according to the invention is the 2-methoxy-4-methoxymethyl-3,5,6-trifluorobenzyl ester of (+)-cis-3-(Z-2-chloro-3,3,3-trifluoroprop-1-en-yl)-2,2-dimethylcyclopropanecarboxylic acid, which is believed to have the (1R, 3R) configuration in the cyclopropane ring.

Other examples of compounds according to the invention include those set out in Table I. The compounds listed in Table I correspond to the formula:

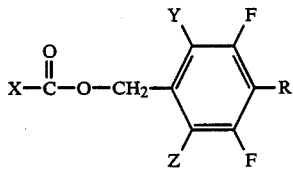

In Table I, values are given for Y, Z, R and X-COOH, where X-COOH describes an acid forming an ester according to the invention; values of X-COOH are expressed as X$^1$ to X$^8$, where X$^1$ to X$^8$ have the meanings given below:

X$^1$: (±)-cis-3-(Z-2-chloro-3,3,3-trifluoroprop-1-en-1-yl)-2,2-dimethylcyclopropanecarboxylic acid;

$X^2$: (±)-trans-3-(Z-2-chloro-3,3,3-trifluoroprop-1-en-1-yl)-2,2-dimethylcyclopropanecarboxylic acid;

$X^3$: (±)-cis/trans-3-(2-methylprop-1-en-1-yl)-2,2-dimethylcyclopropanecarboxylic acid (cis/trans ratio 3:7);

$X^4$: (±)-cis-3-(2,2,-dichloroethenyl)-2,2-dimethylcyclopropanecarboxylic acid;

$X^5$: (±)-trans-3-(2,2-dichloroethenyl)-2,2-dimethylcyclopropanecarboxylic acid;

$X^6$: 2,2,3,3-tetramethylcyclopropanecarboxylic acid;

$X^7$: (±)-trans-3-(2,2-difluoroethenyl)-2,2-dimethylcyclopropanecarboxylic acid;

$X^8$: (±)-cis-3-(2,2-difluoroethenyl)-2,2-dimethycyclopropanecarboxylic acid;

TABLE I

| Product No | X—COOH | Y | Z | R |
|---|---|---|---|---|
| 1 | $X^1$ | $OCH_3$ | F | $CH_3$ |
| 2 | $X^1$ | $OCH_3$ | F | $OCH_3$ |
| 3 | $X^1$ | $OCH_3$ | $OCH_3$ | $CH_3$ |
| 4 | $X^1$ | $OCH_3$ | F | H |
| 5 | $X^1$ | $OCH_3$ | $OCH_3$ | $OCH_3$ |
| 6 | $X^1$ | $OCH_3$ | F | $CH_2CH=CH_2$ |
| 7 | $X^1$ | $OCH_3$ | F | $OC_2H_5$ |
| 8 | $X^1$ | $OCH_3$ | F | $CH_2OCH_3$ |
| 9 | $X^2$ | $OCH_3$ | F | $CH_2OCH_3$ |
| 10 | $X^3$ | $OCH_3$ | F | $CH_2OCH_3$ |
| 11 | $X^4$ | $OCH_3$ | F | $CH_2OCH_3$ |
| 12 | $X^5$ | $OCH_3$ | F | $CH_2OCH_3$ |
| 13 | $X^6$ | $OCH_3$ | F | $CH_2OCH_3$ |
| 14 | $X^1$ | $OC_2H_5$ | F | $OC_2H_5$ |
| 15 | $X^1$ | $OCH_3$ | F | $CH_2C\equiv CH$ |
| 16 | $X^1$ | $OCH_3$ | F | $CH_2OC_2H_5$ |
| 17 | $X^1$ | $OCH_3$ | F | $CH_2C(Cl)=CH_2$ |
| 18 | $X^1$ | $OCH_3$ | F | $CH_2CH=CHCl$ |
| 19 | $X^1$ | $OCH_3$ | $OCH_3$ | $CH_2OCH_3$ |
| 20 | $X^2$ | $OCH_3$ | F | $CH_2C\equiv CH$ |
| 21 | $X^1$ | $OC_2H_5$ | F | $CH_2OCH_3$ |
| 22 | $X^7$ | $OCH_3$ | F | $CH_2OCH_3$ |
| 23 | $X^8$ | $OCH_3$ | F | $CH_2OCH_3$ |

The compounds of the invention according to Formula (I) are esters and may be prepared by conventional esterification processes, of which the following are examples.

(a) An acid of formula (II):

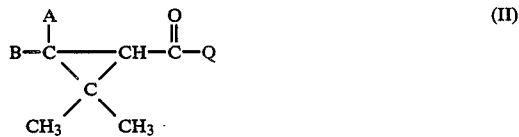

where Q represents the hydroxy group and A and B have any of the meanings given hereinabove, may be reacted directly with an alcohol of formula (III):

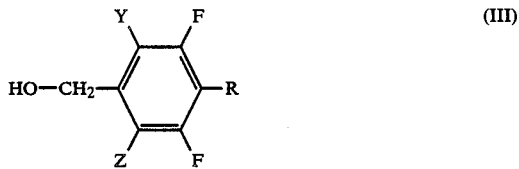

where Y, Z and R have any of the meanings given hereinabove, the reaction preferably taking place in the presence of an acid catalyst, for example, dry hydrogen chloride, or a dehydrating agent, for example a carbodiimide such as dicyclohexylcarbodiimide.

(b) An acid halide of formula (II) where Q represents a halogen atom, preferably a chlorine atom, and A and B have any of the meanings given hereinabove, may be reacted with an alcohol of formula (III), the reaction preferably taking place in the presence or a base, for example, pyridine, a trialkylamine or an alkali metal hydroxide or carbonate.

(c) An acid of formula (II) where Q represents the hydroxy group or, preferably, an alkali metal salt thereof, may be reacted with halide of formula (IV):

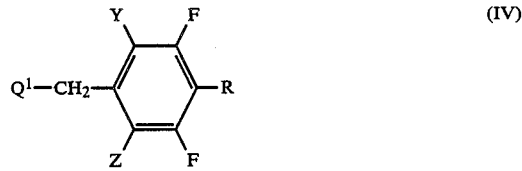

where $Q^1$ represents a halogen atom, preferably the bromine or chlorine atom and Y, Z, and R have any of the meanings given hereinabove, or with the quaternary ammonium salts derived from such halides by reaction with tertiary amines, for example pyridine, or trialkylamines such as triethylamine.

(d) A lower alkyl ester of formula (II) where Q represents a lower alkoxy group containing up to six carbon atoms, preferably the methoxy or ethoxy group, and A and B have any of the meanings given hereinabove, is heated with an alcohol of formula (III) to effect a transesterification reaction. Preferably the process is performed in the presence of a suitable catalyst, for example, an alkali metal alkoxide, such as sodium methoxide, or an alkylated titanium derivative, such as tetramethyl titanate or tetraethyl titanate.

All of these conventional processes for the preparation of esters may be carried out using solvents and diluents for the various reactants where appropriate, and may be accelerated or lead to higher yields of product when performed at elevated temperatures or in the presence of appropriate catalysts, for example phase-transfer catalysts.

The preparation of individual isomers may be carried out in the same manner but commencing from the corresponding individual isomers of compounds of formula (II). These may be obtained by conventional isomer separation techniques from mixtures of isomers. Thus cis and trans isomers may be separated by fractional crystallisation of the carboxylic acids or salts thereof, whilst the various optically active species may be obtained by fractional crystallisation of salts of the acids with optically active amines, followed by regeneration of the optically pure acid. The optically pure isomeric form of the acid (or its equivalent acid chloride or ester) may then be reacted with the alcohol of formula (III) or a halide of formula (IV) to produce a compound of formula (I) in the form of an individually pure isomer thereof.

The preparation of the compounds of formula (II) wherein Q is hydroxy, alkoxy or halo, and A and B are as defind hereinabove, useful as intermediates in the preparation of the compounds of the invention, is fully described in British patent specification No. 2,000,764 and in U.S. Pat. No. 4,183,948, or British patent specification No. 1,413,491.

The compounds of formula (III) and formula (IV) are believed to be novel. Accordingly, in two further aspects, the invention provides a compound of formula (III) wherein Y, Z and R have any of the meanings given hereinbefore and a compound of formula (IV) wherein Y, Z and R have any of the meanings given hereinbefore and $Q^1$ represents halo. Particular examples of compounds according to formula (III) are those for which values of Y, Z and R are listed in Table II.

TABLE II

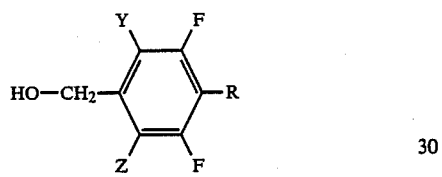

| Compound | Y | Z | R |
|---|---|---|---|
| A | OCH₃ | F | CH₃ |
| B | OCH₃ | F | CH₂OCH₃ |
| C | OCH₃ | F | CH₂CH=CH₂ |
| D | OCH₃ | F | OCH₃ |
| E | OCH₃ | OCH₃ | CH₃ |
| F | OCH₃ | OCH₃ | OCH₃ |
| G | OCH₃ | OCH₃ | CH₂CH=CH₂ |
| H | OCH₃ | OCH₃ | CH₂OCH₃ |
| I | OCH₃ | F | H |
| J | OCH₃ | F | CH₂C≡CH |
| K | OCH₃ | OCH₃ | H |
| L | OCH₃ | OCH₃ | CH₂C≡CH |
| M | OC₂H₅ | F | OC₂H₅ |
| N | OCH₃ | F | CH₂OCH₂CH₃ |
| O | OCH₃ | F | CH₂C(Cl)=CH₂ |
| P | OCH₃ | F | CH₂CH=CHCl |
| Q | OCH₃ | F | OC₂H₅ |
| R | OC₂H₅ | F | CH₂OCH₃ |

The compounds according to formula (III) may be prepared by sequences of reactions, each stage of which is conventional in itself. Examples of processes leading to the preparation of a number of compounds of formula (III) are set out in Schemes I–VII. In each of the schemes, analogous compounds of formula (III) may be prepared using the appropriate starting materials. A key to the reagents employed in the various processes described in the schemes is provided below:

(a) Butyllithium/methyl iodide
(b) Butyllithium/carbon dioxide
(c) Thionyl chloride/methanol
(d) Sodium methoxide(1 eqivalent)/methanol
(e) Lithium borohydride
(f) lithium aluminium hydride
(g) Dihydropyran/H⁺
(h) Butyllithium/allyl bromide
(i) Aqueous methanol/H⁺
(j) Sodium methoxide(2 equivalents)/methanol
(k) Sodium methoxide(3 equivalents)/methanol
(l) N-bromosuccinimide/carbon tetrachloride/light
(m) Potassium carbonate/methyl iodide/methyl ethyl ketone Further details of the process described above and in the Schemes are given in the Examples hereinafter.

SCHEME I

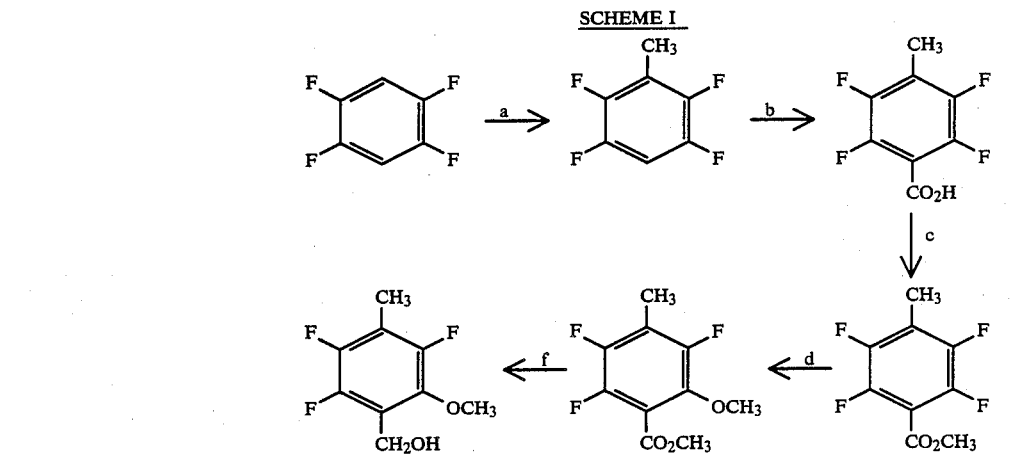

SCHEME II

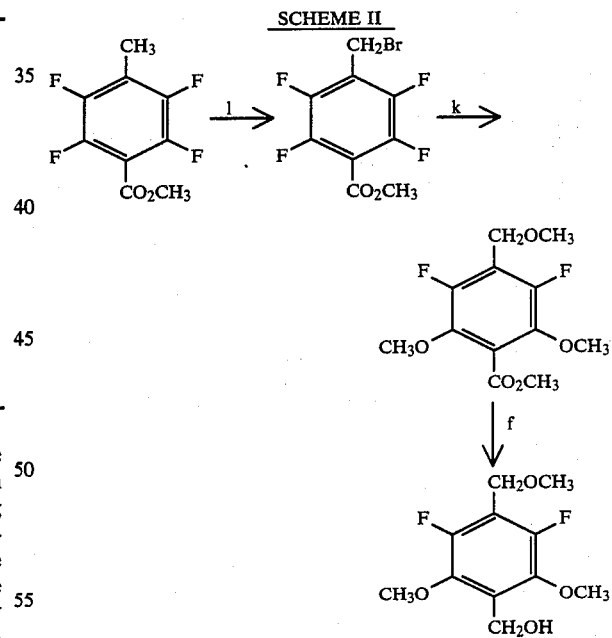

SCHEME III

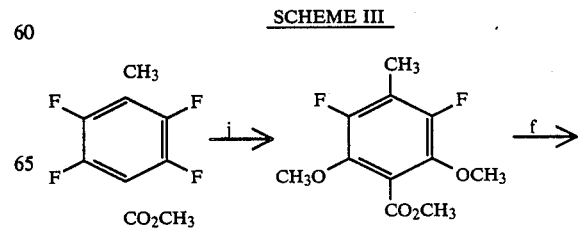

-continued
SCHEME III

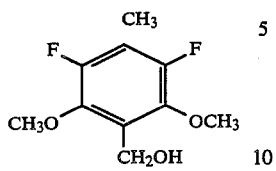

SCHEME IV

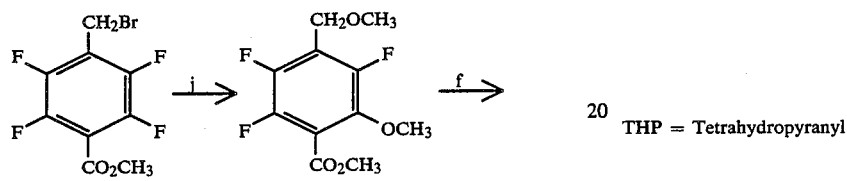

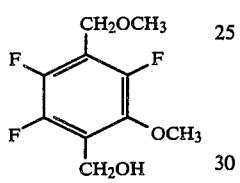

SCHEME V

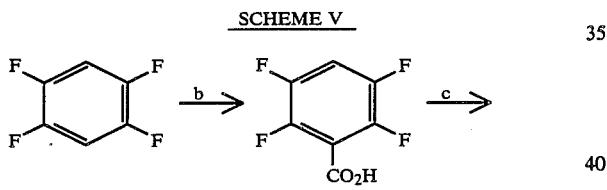

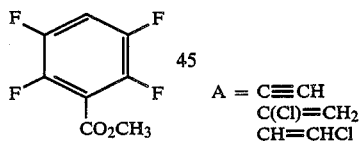

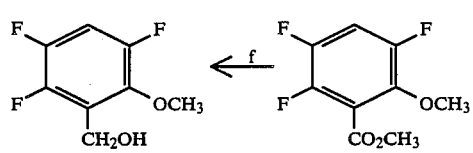

SCHEME VI

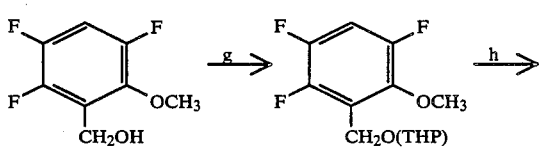

-continued
SCHEME VI

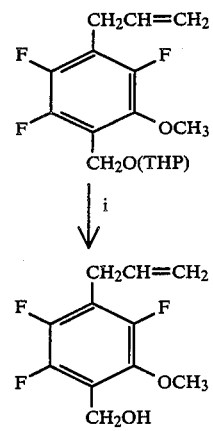

THP = Tetrahydropyranyl

SCHEME VII (i) n-BuLi
(ii) CuBr/DMF
(iii) ACH$_2$Cl

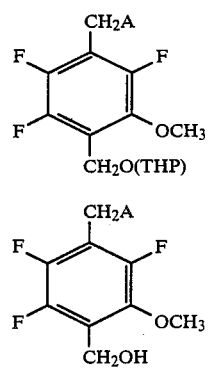

A = C≡CH
C(Cl)=CH$_2$
CH=CHCl

When the processes for preparing the compounds of Formula I are performed using intermediates which are themselves mixtures of isomers the products obtained will also be mixtures of isomers. Thus, the product would be a mixture of (±)-cis and (±)-trans isomers (perhaps with one form predominating) if the intermediate acid or acid derivative was used in the form of a mixture of (±)-cis and (±)-trans isomers. If a single isomer of the acid, eg. the (+)-cis isomer of 3-(Z-2-chloro-3,3,3-trifluoroprop-1-ene-1-yl)-2,2-dimethylcyclopropane carboxylic acid, was used, the product would also be the single isomer of that stereochemical configuration, or a pair of isomers if there is an asymmetric carbon atom in the alcohol moiety.

The compounds of formula (I) may be used to combat and control infestations of insect and acarine pests. The insect and acarine pests which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula (I) suitable inert diluent or carrier materials, and/or surface active agents.

The compounds of the invention may be the sole active ingredient of the composition or they may be admixed with one or more additional active ingredients such as insecticides, insecticide synergist, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compounds of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

(a) Pyrethroids such as permethrin, esfenvalerate, deltamethrin, cyhalothrin, biphenthrin, fenpropathrin, cyfluthrin, tefluthrin, fish safe pyrethroids for example ethofenprox, natural pyrethrins, tetramethrin, s-bioallethrin, fenfluthrin, prallethrin and 5-benzyl-3-furyl-methyl-(E)-(1R, 3S)-2,2-dimethyl-3-(2-oxothiolan-3-ylidenemethyl)cyclopropane carboxylate;

(b) Organophosphates such as profenofos, sulprofos, dichloruos, methyl parathion, azinphos-methyl, demeton-s-methyl, heptenophos, thiometon, fenamiphos, monocrotophos, profenophos, triazophos, methamidophos, dimethoate, phosphamidon, malathion, chlorpyrifos, phosalone, fensulfothion, fonofos, phorate, phoxim, pyrimiphos-methyl, fenitrothion and diazinon;

(c) Carbamates (including aryl carbamates) such as pirimicarb, cloethocarb, carbofuran, ethiofencarb, aldicarb, thiofurox, carbosulfan, bendiocarb, fenobucarb, propoxur and oxamyl;

(d) Benzoyl ureas such as triflumuron, chlorofluazuron;

(e) Organic tin compounds such as cyhexatin, fenbutatin oxide, azocyclotin;

(f) Macrolides such as avermectins or milbemycins, for example such as abamectin, avermectin, and milbemycin;

(g) Hormones and synthetic mimics thereof such as juvenile hormone, juvabione, ecdysones, methoprene and hydroprene.

(h) Pheromones.

(i) Organochlorine compounds such as benzene hexachloride, DDT, chlordane or dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin, can be employed. Alternatively insecticides specific for particular insect species/stages for example ovolarvicides such as clofentezine, amitraz, chlordimeform, flubenzimine, hexythiazox and tetradifon, motilicides such as dicofol or propargite, adulticides such as bromopropylate, chlorobenzilate, or insect growth regulators such as hydramethylon, cyromazine, methoprene, chlorofluazuron and diflubenzuron may also be included in the compositions.

Examples of suitable insecticide synergists for use in the compositions include piperonyl butoxide, sesamex, and dodecyl imidazole.

Suitable herbicides, fungicides and plant growth regulators for inclusion in the compositions will depend upon the intended target and the effect required. An example of a rice selective herbicide which can be included in propanil, an example of a plant growth regulator for use in cotton is "Pix", and examples of fungicides for use in rice include blasticides such as blasticidin-S. The choice of other ingredients to be used in mixture with the active ingredient will often be within the normal skill of the formulator, and will be made from known alternatives depending upon the total effect to be achieved.

The ratio of the compound of the invention to any other active ingredient in the composition will depend upon a number of factors including the type of insect pests to be controlled, and the effects required from the mixture. However, in general, the additional active ingredient of the composition will be applied at about the rate it would usually be employed if used on its own, or at a lower rate if synergism occurs.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material, for example pumice.

Alternatively the compositions may be in the form of liquid preparations to be used as dips, sprays or aerosols. Dips and sprays are generally aqueous dispersions or emulsions of the active ingredient in the presence of one or more known wetting agents, dispersing agents or emulsifying agents (surface active agents). Aerosol compositions may contain the active ingredient or ingredients, a propellant and an inert diluent, for example odourless kerosene or alkylated benzenes. In a preferred form, aerosol compositions may contain from 0.005% to 4% of active ingredient or ingredients, the remainder of the composition comprising a solvent, selected from odourless kerosine and alkylated benzenes, and a propellant. Aerosol compositions may optionally incorporate other additives, for example perfumes or corrosion inhibitors.

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and optionally adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 1-99% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of formula (I) and compositions comprising them are very toxic to wide varities of insect, acarine and other invertebrate pests, including, for example, the following:
*Myzus persicae* (aphids)
*Aphis fabae* (aphids)
*Megoura viceae* (aphids)
*Aedes aegypti* (mosquitos)
Anopheles spp. (mosquitos)
Culex spp. (mosquitos)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)
Aonidiella spp. (scale insects)
Trialeuroides spp. (white flies)
*Blattella germanica* (cockroaches)
*Periplaneta americana* (cockroaches)
*Blatta orientalis* (cockroaches)
*Spodoptera littoralis* (cotton leaf worm)
*Heliothis virescens* (tobacco budworms)
*Chortiocetes terminifera* (locusts)
Diabrotica spp. (rootworms)
Agrotis spp. (cutworms)
*Chilo partellus* (maize stem borers)
*Nilaparvata lugens* (plant hoppers)
*Nephotettix cincticeps* (leaf hoppers)
*Panonychus ulmi*
*Panonychus citri*
*Tetranychus urticae* (red spider mite)
*Tetranychus cinnabarinus* (carmine spider mite)

The compounds according to formula (I) and compositions comprising them have been shown to be particularly useful in controlling lepidopteran pests of cotton, for example Spodoptera spp. and Heliothis spp., and acarine pests such as Tetranychus spp. and Panonychus spp. They have also been shown to be particularly useful in combating pests which inhabit the soil, for example Diabrotica spp. by virtue of their fumigant activity. They have also been shown to exhibit high levels of knockdown activity against public health insect pests such as *Musca domestica* (housefly), *Blattella germanica* (cockroach) and *Aedes aegypti* (mosquito). They may also be useful in combating insect and acarine pests which infest domestic animals, such as *Lucilia sericata* and ixodid ticks such as Boophilus spp., Ixodes spp., Amblyomma spp., Rhipicephalus spp., and Dermaceutor spp. They are effective in combating both susceptible and resistant strains of these pests in their adult, larval and intermediate stages of growth, and may be applied to the infested host animal by topical, oral or parental administration.

The following Examples illustrate various aspects of this invention. In the preparation Examples the products were usually identified and characterised by means of nuclear magnetic resonance (NMR) spectroscopy and infra red (IR) spectroscopy. In each case where a product is specifically named its spectral characteristics are consistent with the assigned structure. Except where stated otherwise, exemplified compounds having one or more asymmetrically substituted carbon atoms were prepared in racemic form.

In the Examples, Gas Liquid Chromatography (GLC) retention times were determined on a Hewlett Packard 5890 Gas Chromatograph, using a Chrompak, CPSil 5CB column of 12.5M length and 0.2 mm internal diameter. Unless otherwise stated, the injection temperature was 100° C., and a temperature gradient of 15° C./minute employed, up to a maximum temperature of 250° C., maintained for 4 minutes. The carrier gas was helium at a column head pressure maintained at 11 psi. Alternative injection and maximum temperatures are indicated in the Examples where appropriate.

$^1$H Nuclear Magnetic Resonance (NMR) spectrometry was performed at a frequency of 270 MHz on a Jeol FX 270 NMR spectrometer, unless otherwise indicated. 90 MHz, 60 MHz and 400 MHz $^1$H NMR spectrometry were performed using Jeol FX 90Q, Jeol PMX 60SI and Jeol GX400 spectrometers respectively.

$^{19}$H NMR spectrometry was performed on a Heol FX90Q spectrometer at a frequency of 84.26 MHz. All NMR shift ($\delta$) values are quoted in ppm relative to a standard (TMS or $CFCl_3$).

Molecular Ion (M+) peaks were determined on one of three mass spectrometers: Jeol DX303, Kratos MS80 or Hewlett Packard HP 5992.

The following Examples illustrate various aspects of the invention.

EXAMPLE 1

This Example illustrates the preparation of 4-methyl-2,3,5,6-tetrafluorobenzoic acid.

A solution of n-butyllithium (2.7M in n-hexane, 21 cm$^3$) was added dropwise to a stirred solution of 2,3,5,6-tetrafluorotoluene (9.0 g) in dry dimethoxymethane cooled to −70° C. under a nitrogen atmosphere and the mixture stirred for one hour. Carbon dioxide was then passed into the mixture for 3 hours during which time a white solid precipitate formed. After allowing the mixture to attain the ambient temperature (ca. 22° C.) it was poured into water. The resultant mixture was acidified with dilute hydrochloric acid and extracted with diethyl ether. The ethereal extract was washed with water and dried over anhydrous magnesium sulphate. Removal of the solvent yielded a semi solid residue which on trituration with petroleum ether (boiling range 40°-60° C.) gave 4-methyl-2,3,5,6-tetrafluorobenzoic acid (2.5 g) white crystals, mp 168° C. (Infra red C=O, 1700 cm$^{-1}$.)

EXAMPLE 2

This Example illustrates the preparation of methyl 4-methyl-2,3,5,6-tetrafluorobenzoate.

A stirred mixture of 4-methyl-2,3,5,6-tetrafluorobenzoic acid (1.0 g) and thionyl chloride (10 cm$^3$) was heated at the reflux temperature for 2 hours. The residue remaining after removal of excess thionyl chloride by evaporation under reduced pressure was treated with dry methanol (20 cm$^3$) for 1 hour at the ambient temperature (ca. 22° C.). The excess methanol was then removed by evaporation under reduced pressure to yield a residue of substantially pure methyl 4-methyl-2,3,5,6-tetrafluorobenzoate (1.0 g). (Infra red C=O, 1735 cm$^{-1}$.)

EXAMPLE 3

This Example illustrates the preparation of methyl 2-methoxy-4-methyl-3,5,6-trifluorobenzoate.

Methyl 4-methyl-2,3,5,6-tetrafluorobenzoate (1.0 g) was added to a solution of sodium methoxide obtained by dissolving sodium metal (0.15 g) in dry methanol (15 cm$^3$) and the mixture heated at the reflux temperature for 2 hours until the reaction was complete. The product was purified by h.p.l.c. (Gilson) using a silica column and as eluent a mixture of petroleum ether (boiling range 40°-60° C., 1800 cm$^3$) and diethyl ether (200 cm$^3$), to obtain methyl 2-methoxy-4-methyl-3,5,6-trifluorobenzoate (0.38 g).

100 MHz N.m.r. (CDCl$_3$): 2.28 (t, 3H); 4.00 (s, 6H).
Infra red (liquid film): 1730, 1480, 1300 cm$^{-1}$

EXAMPLE 4

This Example illustrates the preparation of 2-methoxy-4-methyl-3,5,6-trifluorobenzyl alcohol (Compound A).

Lithium aluminium hydride (0.5 g) was added to a stirred solution of methyl 2-methoxy-4-methyl-3,5,6-trifluorobenzoate (6.2 g) in sodium dried diethyl ether (50 cm$^3$) and the mixture stirred for a further three hours. The mixture was then stood at the ambient temperature for a further 17 hours. After pouring the mixture into water and acidifying with dilute hydrochloric acid the resultant mixture was extracted with diethyl ether. The ethereal extracts were washed with water and dried over anhydrous magnesium sulphate. Removal of the solvent by evaporation under reduced pressure yielded 2-methoxy-4-methyl-3,5,6-trifluorobenzyl alcohol (5.0 g) as a low melting white solid.

100 MHz N.m.r. (CDCl$_3$): 2.24 (t, 3H); 2.85 (s, 1H); 4.00 (s, 3H); 4.76 (s, 2H).

EXAMPLE 5

This Example illustrates the preparation of methyl 3,5-difluoro-2,6-dimethoxy-4-methylbenzoate.

Methyl 4-methyl-2,3,5,6-tetrafluorobenzoate (2.0 g) was added to a stirred solution of sodium methoxide in methanol (obtained by dissolving sodium metal (0.5 g) in dry methanol (20 cm$^3$) and the mixture heated at the reflux temperature until the starting material could no longer be detected by thin layer chromatographic analysis. (Silica plate, dichloromethane eluent.) After removal of the solvent by evaporation under reduced pressure the residual material was dissolved in diethyl ether, and the solution washed with water and dried over anhydrous magnesium sulphate. Removal of the ether by evaporation under reduced pressure yielded a mixture of the desired product and the monomethoxylated product of Example 3. Purification was effected by the use of h.p.l.c. (Gilson) using a silica column and as eluent a mixture of petroleum ether (boiling range 40°-60° C., 1800 cm$^3$) and diethyl ether (200 cm$^3$) to yield methyl 3,5-difluoro-2,6-dimethoxy-4-methylbenzoate (0.75 g) as an oil.

100 MHz N.m.r. (CDCl$_3$): 2.23 (t, 3H); 3.95 (d, 9H).
Infra red (liquid film): 1730 cm$^{-1}$

EXAMPLE 6

This Example illustrates the preparation of 3,5-difluoro-2,6-dimethoxy-4-methylbenzyl alcohol (Compound E).

Lithium aluminium hydride (0.124 g) was added in a single portion to a solution of methyl 3,5-difluoro-2,6-dimethoxy-4-methylbenzoate (0.754 g) in dry diethyl ether (15 cm$^3$) and the mixture stirred for one hour at the ambient temperature. Ethyl acetate was then added to decompose any remaining hydride, after which water was added and the mixture acidified with dilute hydrochloric acid. After extracting the mixture with diethyl ether, the extracts were dried over anhydrous magnesium sulphate and then concentrated by removal of the solvent by evaporation under reduced pressure to yield 3,5-difluoro-2,6-dimethoxy-4-methylbenzyl alcohol (0.66 g) which solidified on standing (mp. 80°-81° C.).

100 MHz N.m.r. (CDCl$_3$): 2.20 (t, 3H); 2.94 (s, 1H); 3.95 (s, 6H); 4.70 (s, 2H)

EXAMPLE 7

This Example illustrates the preparation of 2,3,5,6-tetrafluorobenzoic acid.

n-Butyllithium (2.7M solution in n-hexane, 148 cm$^3$) was added dropwise over a period of one hour to a stirred solution of 2,3,5,6-tetrafluorobenzene (60 g) in dry tetrahydrofuran (200 cm$^3$) maintained at −70° C. under a nitrogen atmosphere, after which the mixture was stirred at −70° C. for a further one hour. Carbon dioxide gas was passed into the mixture over a period of 4 hours during which time the temperature was allowed to warm up to the ambient value (ca. 22° C.). After adding water and acidifying with dilute hydrochloric acid, the mixture was extracted with diethyl ether and the extracts dried over anhydrous magnesium sulphate. The product was obtained by removal of the solvent by evaporation under reduced pressure to give 2,3,5,6-tetrafluorobenzoic acid (42.5 g), mp. 152°-154° C.

90 MHz N.m.r. (CDCl$_3$+DMSO): 7.3–7.7 (m, 1H); 10.75 (broad s, 1H).

EXAMPLE 8

This Example illustrates the preparation of methyl 2,3,5,6-tetrafluorobenzoate.

A mixture of 2,3,5,6-tetrafluorobenzoic acid (25 g) and thionyl chloride (40 cm$^3$) was heated at the reflux temperature for 3 hours after which the excess thionyl chloride was removed by evaporation under reduced pressure to leave a residue of 1-chlorocarbonyl-2,3,5,6-tetrafluorobenzene. To this was added an excess of dry methanol and the mixture stirred for one hour at the ambient temperature. Removal of excess methanol by evaporation under reduced pressure gave methyl 2,3,5,6-tetrafluorobenzoate (19 g) as a mobile liquid.

90 MHz N.m.r. (CDCl$_3$): 4.00 (s, 3H); 7.0–7.4 (m, 1H).

Infra red (liquid film): 1730 cm$^{-1}$

EXAMPLE 9

This Example illustrates the preparation of methyl 2-methoxy-3,5,6-trifluorobenzoate.

Methyl 2,3,5,6-tetrafluorobenzoate (17 g) was added to a solution of sodium methoxide (obtained by dissolving sodium metal (1.8 g) in dry methanol (70 cm$^3$) and the mixture heated at the reflux temperature for 2 hours. The excess methanol was removed by evaporation under reduced pressure and the residue partitioned between diethyl ether and water. After washing the ethereal phase with water and drying over anhydrous magnesium sulphate, removal of the solvent by evaporation under reduced pressure yielded a liquid residue (13 g) which was purified by h.p.l.c. (Gilson) using the conditions set out in Example 5 to give methyl 2-methoxy-3,5,6-trifluorobenzoate (10.9 g) as an oil.

90 MHz N.m.r. (CDCl$_3$): 3.96 (s, 6H); 6.9–7.27 (m, 1H).

$^{19}$F N.m.r. (CDCl$_3$): −131, −140, −143.

Infra red (liquid film): 1730 cm$^{-1}$

EXAMPLE 10

This Example illustrates the preparation of 2-methoxy-3,5,6-trifluorobenzyl alcohol (Compound I).

Lithium aluminium hydride (1.5 g) was added in portions to a stirred mixture of methyl 2-methoxy-3,5,6-trifluorobenzoate (10.9 g) in dry diethyl ether (80 cm$^3$) over a period of 30 minutes at the ambient temperature and the resultant mixture stirred for a further period of 30 minutes. The product, 2-methoxy-3,5,6-trifluorobenzyl alcohol (8.8 g), was isolated by a similar procedure to that illustrated in Example 6.

100 MHz N.m.r. (CDCL$_3$): 2.7 (broad s, 1H); 3.95 (s, 3H); 4.7 (s, 2H); 6.9(m, 1H)

Infra red (liquid film): 3300 cm$^{-1}$

EXAMPLE 11

This Example illustrates the preparation of 2-(2-methoxy-3,5,6-trifluorobenzyloxy)tetrahydropyran. A stirred mixture of 2-methoxy-3,5,6-trifluorobenzyl alcohol (8.8 g), dihydropyran (4.62 g) and dry diethyl ether (50 cm$^3$) was treated with concentrated hydrochloric acid (ca. 0.5 cm$^3$) and kept at the ambient temperature for 24 hours. Removal of the volatile portion of the mixture by evaporation under reduced pressure yielded 2-(2-methoxy-3,5,6-trifluorobenzyloxy)tetrahydropyran (13.2 g) as a mobile liquid.

100 MHz N.m.r. (CDCl$_3$): 1.7 (m, 6H); 3.7 (m, 1H); 3.95 (s, 4H); 4.5–4.95 (m, 3H); 7.0 (m, 1H)

EXAMPLE 12

This Example illustrates the preparation of 2-(4-allyl-2-methoxy-3,5,6-trifluorobenzyloxy)tetrahydropyran.

A solution of n-butyllithium (2.7M in n-hexane, 1.1 cm$^3$) was added carefully to a stirred solution of 2-(2-methoxy-3,5,6-trifluorobenzyloxy)tetrahydropyran (0.8 g) in dry tetrahydrofuran (10 cm$^3$) maintained at a temperature of −70° C. under a nitrogen atmosphere and the mixture thereafter warmed to −65° C. and stirred for one hour. Allyl bromide (1.0 g) was then added to the mixture which was then stirred for 4 hours during which time the mixture was allowed to warm to the ambient temperature (ca. 22° C.). Water was added to the mixture which was then extracted with diethyl ether. The extracts were dried over anhydrous magnesium sulphate and concentrated by evaporation of the solvent under reduced pressure. The residue consisted of the desired product, 2-(4-allyl-2-methoxy-3,5,6-trifluorobenzyloxy)tetrahydropyran contaminated with a little starting material.

100 MHz N.m.r. (CDCL$_3$): 1.7 (m, 6H); 3.5 (m, 2H); 3.55(m, 1H); 3.95 (s, 4H); 4.4–5.3 (m, 5H); 5.9 (m, 1H)

EXAMPLE 13

This Example illustrates the preparation of 4-allyl-2-methoxy-3,5,6-trifluorobenzyl alcohol (Compound C).

The product of Example 12, consisting mainly of 2(4-allyl-2-methoxy-3,5,6-trifluorobenzyloxy)tetrahydropyran (0.5 g) was dissolved in a mixture of methanol (5.0 cm$^3$) and dilute hydrochloric acid (2.0 cm$^3$) and the mixture stirred at the ambient temperature (ca. 22° C.) for 30 minutes. After the removal of the volatile portion by evaporation under reduced pressure the residue was partitioned between water and diethyl ether and the ethereal phase separated, washed with water and dried over anhydrous magnesium sulphate. Removal of the solvent by evaporation under reduced pressure yielded an oil (0.3 g) which was purified by h.p.l.c. (Gilson) using a silica column and as eluent a mixture of petroleum ether (boiling range 40°–60° C., one part by volume) and diethyl ether (1 part by volume) to give pure 4-allyl-2-methoxy-3,5,6-trifluorobenzyl alcohol (0.26 g).

100 MHz N.m.r. (CDCl$_3$): 2.8 (bs, 1H); 3.4 (m, 2H); 3.95 (s, 3H); 4.65 (s, 2H); 4.95 (m, 1H); 5.1 (m, 1H) 5.8 (m, 1H)

EXAMPLE 14

This Example illustrates the preparation of methyl 2-methoxy-4-methoxymethyl-3,5,6-trifluorobenzoate as a by-product in the preparation of methyl 4-methoxymethyl-2,3,5,6-tetrafluorobenzoate.

Methyl 4-bromomethyl-2,3,5,6-tetrafluorobenzoate (10 g, prepared according to the method described in U.S. Pat. No. 4,370,346) was dissolved in dry methanol (10 cm$^3$) and the solution added dropwise to a solution of sodium methoxide in dry methanol obtained by dissolving sodium metal (1.5 g) in dry methanol (20 cm$^3$) at the ambient temperature (ca. 22° C.). When the addition was completed the excess methanol was removed by evaporation under reduced pressure. Water was added and the mixture acidified with dilute hydrochloric acid and extracted with ethyl acetate. After drying the extracts over anhydrous magnesium sulphate and removing the solvent by evaporation under reduced pressure, the residue, which partially solidified, was triturated with petroleum ether (boiling range 40°-60° C.) and the solid separated by filtration. The solid (4.0 g) was shown by n.m.r. and infra-red analysis to be 4-methoxymethyl-2,3,5,6-tetrafluorobenzoic acid, mp. 92°-95° C. after recrystallisation from a petroleum ether/chloroform mixture.) The filtrate was washed with dilute sodium hydroxide solution and with water, separated, dried over anhydrous magnesium sulphate and concentrated by evaporation under reduced pressure to give a residue (1.4 g) which was purified by h.p.l.c. (Gilson) using a silica column and as eluent a mixture of petroleum ether (boiling range 40°-60° C. 3 parts by volume) and diethyl ether (one part by volume) to yield a faster running product (0.6 g) and a slower running product (0.65 g). These were shown by n.m.r. spectroscopy to be methyl 4-methoxymethyl-2,3,5,6-tetrafluorobenzoate (A) and methyl 2-methoxy-4-methoxymethyl-3,5,6-trifluorobenzoate (B) respectively.

90 MHz N.m.r (CDCl$_3$): (A) 3.41 (s, 3H); 3.99 (s, 3H); 4.60 (t, 2H). (B) 3.40 (s, 3H); 3.96 (s, 6H); 4.57 (t, 2H).

EXAMPLE 15

This Example illustrates the preparation of 2-methoxy-4-methoxymethyl-3,5,6-trifluorobenzyl alcohol (Compound B).

A mixture of methyl 2-methoxy-4-methoxymethyl-3,5,6-trifluorobenzoate (6.2 g), lithium aluminium hydride (0.5 g) and dry diethyl ether (50 cm$^3$) was stirred for two hours and kept at the ambient temperature for a further sixteen hours after which the desired product was isolated by the procedure illustrated in Example 4. 2-Methoxy-4-methoxymethyl-3,5,6-trifluorobenzyl alcohol (5.9 g) was identified by n.m.r. and infra red spectroscopy.

EXAMPLE 16

This Example illustrates the preparation of 4-methoxy-2,3,5,6-tetrafluorobenzoic acid.

Pentafluorobenzoic acid (2.2 g) was added to a stirred solution of sodium methoxide [obtained by dissolving sodium metal (0.7 g) in dry methanol (50 cm$^3$)] and the mixture heated at the reflux temperature for 6 hours. The reaction mixture was cooled and stood at the ambient temperature (ca 20° C.)for 17 hours.

The resulting mixture was acidified with concentrated hydrochloric acid and partitioned between diethyl ether and water. The etheral layer was washed with water and dried over anhydrous magnesium sulphate. Removal of the solvent by evaporation under reduced pressure yielded a white solid, which was recrystallized from hexane containing 2% ethyl acetate to give the title compound (1.6 g).

Melting Point: 122°-124° C.

90 MHz N.m.r. (CDCl$_3$): 4.1 (t); 10.5 (broad s).

$^{19}$F N.m.r (CDCl$_3$): −141 (d); −159 (d)

EXAMPLE 17

This Example illustrates the preparation of methyl 4-methoxy-2,3,5,6-tetrafluorobenzoate.

4-methoxy-2,3,5,6-tetrafluorobenzoic acid (1.1 g) was added portionwise to stirred thionyl chloride (10 cm$^3$). The reaction mixture was heated at the reflux temperature for 3 hours. The excess thionyl chloride was removed by evaporation under reduced pressure and the resulting residue was treated with methanol (50 cm$^3$).

The excess methanol was removed by evaporation under reduced pressure to give the title compound (1 g) as an oil.

Infra Red (Liquid film) 1730 cm$^{-1}$

EXAMPLE 18

This Example illustrates the preparation of methyl 2,4-dimethoxy-3,5,6-trifluorobenzoate.

Methyl 4-methoxy-2,3,5,6-tetrafluorobenzoate (1.0 g) was added to a stirred solution of sodium methoxide in methanol [obtained by dissolving sodium metal (0.11 g) in dry methanol (20 cm$^3$)].

The mixture was heated at the reflux temperature for 2 hours, then cooled to the ambient temperature and the excess methanol removed by evaporation under reduced pressure. The residue was partitioned between diethyl ether and water and the ethereal layer washed with water and dried over anhydrous magnesium sulphate.

Evaporation of the solvent under reduced pressure yielded an oil (0.76 g) containing methyl 2,4-dimethoxy-3,5,6-trifluorobenzoate (80%) and methyl 2,4,6-trimethoxy-3,5-difluorobenzoate (16%). Purification of the crude product was achieved by HPLC (Gilson), eluting with Hexane containing 10% by volume diethyl ether.

The first component to be eluted contained methyl 2,4-dimethyl-3,5,6-trifluorobenzoate (0.5 g), for which characteristic data are recorded below, and the second component to be eluted contained methyl 2,4,6-trimethoxy-3,5-difluorobenzoate (0.19 g).

90 MHz N.m.r (CDCl$_3$) 3.95 (s, 6H) 4.1 (t, 3H).

$^{19}$F N.m.r −141 (dd, J=8.3 and 20.9 Hz); −151 (d, J=8.3 Hz); −159 (d, J=20.9 Hz).

EXAMPLE 19

This Example illustrates the preparation of 2,4-dimethoxy-3,5,6-trifluorobenzyl alcohol (Compound D).

Lithium borohydride (0.052 g) was added to a stirred solution of methyl 2,4-dimethoxy-3,5,6-trifluorobenzoate (0.5 g) in dry diethyl ether (10 cm$^3$) and the mixture was stirred at the ambient temperature (ca 20° C.) for 2 hours.

The reaction mixture was poured into water, acidified with dilute hydrochloric acid and the aqueous mixture was extracted with diethyl ether. The ethereal layer was washed with water and dried over anhydrous magnesium sulphate. Removal of the solvent by evaporation under reduced pressure yielded an oil (0.38 g), which was purified by flash column chromatography on a silica support, eluting with dichloromethane to give the title compound as a white solid (0.28 g).

100 MHz N.m.r (CDCl$_3$) 2.4 (bs, 1H); 4.0 (s, 3H); 4.1 (s, 3H); 4.7 (s, 2H)

EXAMPLE 20

This Example illustrates the preparation of methyl 2,4,6-trimethoxy-3,5-difluorobenzoate.

Methyl 4-methoxy-2,3,5,6-tetrafluorobenzoate (2.82 g) was added to a stirred solution of sodium methoxide in methanol [obtained by dissolving sodium metal (0.81 g) in dry methanal (20 cm$^3$)] and the mixture was heated at the reflux temperature for 2 hours.

The reaction was cooled to the ambient temperature and the excess methanol removed by evaporation under reduced pressure. The residue was partitioned between diethyl ether and water and the ethereal layer separated and washed with water, then dried over anhydrous magnesium sulphate.

Evaporation of the solvent gave the title compound (1.2 g), which was used in the following example without further purification.

EXAMPLE 21

This Example illustrates the preparation of 2,4,6-trimethoxy-3,5-difluorobenzyl alcohol (Compound F).

Lithium aluminium hydride (0.2 g) was added to a stirred solution of methyl 2,4-dimethoxy-3,5,6-trifluorobenzoate (1.2 g) in dry diethyl ether (10 cm$^3$) and stirring was continued at the ambient temperature (ca 20° C.) for 1 hour.

The reaction mixture was poured into water, acidified with dilute hydrochloric acid and the aqueous mixture was extracted with diethyl ether. The ethereal layer was washed with water and dried over magnesium sulphate. Removal of the solvent by evaporation under reduced pressure gave an oil (1.0 g) which was purified by flash chromatography on a silica support, eluting with dichloromethane, to give the title compound (0.9 g) as a white solid.

90 MHz N.m.r (CDCl$_3$) 2.1 (s, H); 3.94 (s, 6H); 4.0 (s, 3H); 4.68 (s, 2H)

EXAMPLE 22

This Example illustrates the preparation of 2-(4-propargyl-2-methoxy-3,5,6-trifluorobenzyloxy)tetrahydropyran.

A solution of n-Butyllithium (2.5M in n hexane, 1.7 cm$^3$) was added dropwise over 30 minutes to a stirred solution of 2-(2-methoxy-3,5,6-trifluorobenzyloxy)tetrahydropyran (1.2 g) in dry tetrahydrofuran (10 cm$^3$) maintained at a temperature of −70° C. under a nitrogen atmosphere.

Copper (I) bromide dimethyl sulphide complex (1.0 g) was then added to the stirred mixture in one addition. The mixture was allowed to warm to −30° C. over a period of 15 minutes before being again cooled to −70° C., when propargyl chloride (1 cm$^3$) was added dropwise over a period of 5 minutes; the mixture was then allowed to warm to the ambient temperature, ammonium chloride was added to the mixture which was then extracted with diethyl ether. The ethereal extracts were dried over anhydrous magnesium sulphate and concentrated by evaporation of the solvent under reduced pressure. The residue (0.75 g) contained the expected product (70%) and unreacted starting material (13%). Purification of the crude product was achieved by HPLC (Gilson) eluting with Hexane containing 10% by volume diethyl ether to give the title compound (0.40 g).

Infra Red (Liquid Film): 3300 cm$^{-1}$

N.m.r (CDCl$_3$) 1.5–1.9 (m, 6H); 2.05 (t, 1H); 3.60 (s, 3H); 3.95 (s, 4H); 4.55 (d, 1H); 4.8 (m, 2H)

EXAMPLE 23

4-Propargyl-2-methoxy-3,5,6-trifluorobenzyl alcohol (Compound J) was prepared from 2-(4-propargyl-2-methoxy-3,5,6-trifluorobenzyloxy)tetrahydropyran using the method of Example 13.

N.m.r (CDCl$_3$) 1.6 (broad s, 1H); 2.05 (t, 1H); 3.60 (s, 2H); 4.00 (s, 3H); 4.76 (s, 2H);

EXAMPLE 24

This Example illustrates the preparation of ethyl 2,4-diethoxy-3,5,6-trifluorobenzoate.

Ethyl pentafluorobenzoate (3.6 g) was added to a stirred solution of sodium ehtoxide [prepared by dissolving sodium metal (0.7 g) in ethanol (50 cm$^3$)]. The mixture was heated at the reflux temperature for 3 hours, then allowed to cool to the ambient temperature (ca 20° C.). The solvent was evaporated under reduced pressure and the residue was partioned between water and diethylether. The ethereal layer was separated, dried over anhydrous magnesium sulphate, and concentrated by evaporation under reduced pressure to give a residue (1.3 g) containing 80% of the desired product and 20% of triethoxylated material. The title compound (0.6 g) was isolated by HPLC (Gilson) eluting with hexane containing 10% by volume diethyl ether.

EXAMPLE 25

2,4-diethoxy-3,5,6-trifluorobenzyl alcohol (Compound M) was prepared from ethyl 2,4-diethoxy-3,5,6-trifluorobenzoate using the method of Example 6.

$^{19}$F N.m.r (CDCl$_3$): −147.032 to −147.417 (dd, 1F); −150.496 to −150.620 (d, 1F); −158.481 to −158.742 (d, 1F);

EXAMPLE 26

This Example illustrates the preparation of 4-methoxymethyl-2-ethoxy-3,5,6-trifluorobenzyl alcohol (Compound R).

Lithium Aluminium hydride (0.1 g) was added to a stirred solution of methyl 2-ethoxy-4-methoxymethyl-3,5,6-trifluorobenzoate (0.6 g) and the mixture was stirred at the ambient temperature (ca 20° C.) for 3 hours.

The reaction mixture was then heated at the reflux temperature for 3 hours before being cooled to the ambient temperature and stood for 17 hours.

The mixture was poured into water, acidified with dilute hydrochloric acid and extracted with diethyl ether.

The etheral layer was washed with water and dried over anhdyrous magnesium sulphate. Evaporation of the solvent under reduced pressure gave 4-methoxymethyl-2-ethoxy-3,5,6-trifluorobenzyl alcohol (0.19 g) as an oil.

100 MHz N.m.r (CDCl$_3$): 1.35 (t, 3H); 2.5 (bs, 1H); 3.35 (s, 3H); 4.15 (q, 2H); 4.45 (s, 2H); 4.65 (s, 2H);

EXAMPLE 27

This Example illustrates the preparation of 2-methoxy-4-methoxymethyl-3,5,6-trifluorobenzyl(±)-cis-3-(Z-2-chloro-3,3,3-trifluoroprop-1-en-1-yl)-2,2-dimethylcyclopropanecarboxylate (Product No 8).

A solution of (±)-cis-1-chlorocarbonyl-3-(Z-2-chloro-3,3,3trifluoroprop-1-en-1-yl)-2,2-dimethylcyclopropane (0.39 g) in dry diethyl ether (5 cm$^3$) was added dropwise to a stirred mixture of 2-methoxy-4-methoxymethyl-3,5,6-trifluorobenzyl alcohol (0.37 g), triethylamine (0.16 g) and dry diethyl ether (15 cm$^3$) at the ambient temperature (ca. 22° C.). Stirring was continued for a further one hour after which the precipitated solid was removed by filtration and the filtrate concentrated by evaporation of the solvent under reduced pressure. The residue was purified by column chromatography (silica column eluted with a mixture of petroleum ether (boiling range 40°-60° C.) and diethyl ether (equal volumes)) to yield 2-methoxy-4-methoxymethyl-3,5,6-trifluorobenzyl(±)-cis-3-(Z-2-chloro-3,3,3-trifluoropropl-en-1-yl)-2,2-dimethylcyclopropane carboxylate.

90 MHz N.m.r. (CDCl$_3$): 1.30 (d, 6H); 1.85–2.3 (m, 2H); 3.41 (s, 3H); 3.93 (d, 3H); 4.57 (t, 2H); 5.20 (d, 2H); 6.90 (d, 1H);

EXAMPLE 28

By the use of a procedure similar to that illustrated in the previous Example the following compounds were prepared by reacting the cyclopropane acid chloride with the appropriate benzyl alcohol.

(i) 2-methoxy-4-methyl-3,5,6-trifluorobenzyl($\pm$)-cis-3-(Z-2-chloro-3,3,3-trifluoroprop-1-en-1-yl)-2,2-dimethylcyclopropanecarboxylate (Product No 1).

100 MHz N.m.r. (CDCL$_3$): 1.32 (d, 6H); 2.00 (t, 1H); 2.3 (m, 4H); 3.95 (s, 3H); 5.22 (s, 2H); 6.94 (d, 1H)

(ii) 2,4-dimethoxy-3,5,6-trifluorobenzyl ($\pm$)-cis-3-(Z-2-chloro-3,3,3-trifluoroprop-1-en-1-yl)-2,2-dimethylcyclopropane carboxylate (Product No. 2).

90 MHz N.m.r. (CDCl$_3$): 1.3 (d, 6H): 1.95 (d, 1H); 2.20 (t, 1H; 3.95 (d, 3H); 4.05 (t, 3H); 5.17 (s, 2H); 6.9 (d, 1H)

(iii) 2-methoxy-3,5,6-trifluorobenzyl ($\pm$)-cis-3-(Z-2-chloro-3,3,3-trifluoroprop-1-en-1-yl)-2,2-dimethylcyclopropanecarboxylate (Product No 4).

100 MHz N.m.r (CDCl$_3$): 1.3 (d, 6H); 2.1 (m, 2H); 3.9 (d, 3H); 5.2 (d, 2H); 6.9 (m, 2H)

(iv) 3,5-difluoro-2,4,6-trimethoxybenzyl ($\pm$)-cis-3-(Z-2-chloro-3,3,3-trifluoroprop-1-en-1-yl)-2,2-dimethylcyclopropanecarboxylate (Product No 5).

100 MHz N.m.r (CDCl$_3$): 1.3 (d, 6H); 2.1 (m, 2H); 3.9 (s, 6H); 4.04 (s, 3H); 5.15 (s, 2H); 6.9 (d, 1H)

(v) 4-allyl-2-methoxy-3,5,6-trifluorobenzyl ($\pm$)-cis-3-(Z-2-chloro-3,3,3-trifluoroprop-1-en-1-yl)-2,2-dimethylcyclopropanecarboxylate (Product No 6).

100 MHz N.m.r. (CDCl$_3$): 1.3 (d, 6H); 1.9–2.3 (m, 2H); 3.48 (m, 2H); 3.93 (d, 3H); 5.0–5.3 (m, 4H); 5.95 (m, 1H); 6.95 (d, 1H)

(vi) 3,5-difluoro-2,6-dimethoxy-4-methylbenzyl ($\pm$)-cis-3-(Z-2-chloro-3,3,3-trifluoroprop-1-en-1-yl)-2,2-dimethylcyclopropanecarboxylate (Product No 3).

100 MHz N.m.r. (CDCl$_3$): 1.30 (d, 6H); 2.00 (t, 1H); 2.20 (m, 4H); 3.85 (s, 6H); 4.97 (s, 2H); 6.9 (d, 1H) .

(vii) 3,5,6-Trifluoro-2-methoxy-4-methoxymethylbenzyl ($\pm$)-cis-3-(2,2-dichloroethenyl)-2,2-dimethylcyclopropanecarboxylate (Product No 11).

90 MHz N.m.r (CDCl$_3$): 1.20 (s, 3H); 1.26 (s, 3H); 1.75–2.1 (m, 2H); 3.41 (s, 3H); 3.95 (d, 3H); 4.57 (t, 2H); 5.19 (d, 2H); 6.25 (d, 1H).

(viii) 3,5,6-trifluoro-2-methoxy-4-methoxymethylbenzyl ($\pm$)-trans-3-(2,2-dichloroethenyl)-2,2-dimethycyclopropanecarboxylate (Product No 12).

90 MHz N.m.r (CDCl$_3$): 1.15 (s, 3H); 1.25 (s, 3H); 1.60 (d, 1H); 2.25 (q, 1H); 3.4 (s, 3H); 3.95 (d, 3H); 4.55 (t, 2H); 5.20 (d, 2H); 5.60 (d, 1H)

(ix) 3,5,6-trifluoro-2-methoxy-4-methoxymethylbenzyl 2,2,3,3-tetramethylcyclopropanecarboxylate (Product No 13)

90 MHz N.m.r (CDCl$_3$): 1.20 (d, 13H); 3.4 (s, 3H); 3.95 (d, 3H); 4.55 (t, 2H); 5.2 (d, 2H)

(x) 3,5,6-trifluoro-2-methoxy-4-propargylbenzyl ($\pm$)-cis-3-(Z-2-chloro-3,3,3-trifluoroprop-1-en-1-yl)-2,2-dimethylcyclopropanecarboxylate (Product No 15)

N.m.r (CDCl$_3$): 1.31 (d, 6H); 1.95 (d, 1H); 2.15 (t, 1H); 2.17 (t, 1H); 3.60 (s, 2H); 3.94 (s, 3H); 5.20 (s, 2H); 6.90 (d, 1H).

(xi) 3,5,6-trifluoro-2-methoxy-4-propargylbenzyl ($\pm$)-trans-3-(Z-2-chloro-3,3,3-trifluoroprop-1-en-1-yl)-2,2-dimethylcyclopropanecarboxylate (Product No 20).

N.m.r (CDCl$_3$): 1.22 (s, 3H); 1.35 (s, 3H); 1.75 (d, 1H) 2.05 (t, 1H); 2.42 (q, 1H); 3.60 (s, 2H); 3.96 (s, 3H); 5.22 (s, 2H); 6.12 (d, 1H)

(xii) 3,5,6-trifluoro-2-methoxy-4-methoxymethylbenzyl ($\pm$)-cis/trans-3-(2-methylprop-1-en-1-yl)-2,2-dimethylcyclopropanecarboxylate, cis:trans ratio 3:7 (Product No 10).

100 MHz N.m.r (CDCl$_3$): 1.0–1.4 (m, 7H); 1.65 (s, 6H); 2.0 (t, 1H); 3.4 (s, 3H); 3.9 (d, 3H); 4.55 (t, 2H); 4.82 (d, 1H); 5.2 (t, 2H)

(xiii) 3,5,6-trifluoro-2,4-diethoxybenzyl ($\pm$)-cis-3-(Z-2-chloro-3,3,3-trifluoroprop-1-en-1-yl)-2,2-dimethylcyclopropanecarboxylate (Product No 14)

90 MHz N.m.r (CDCl$_3$): 1.2–1.65 (m, 12H); 1.9–2.3 (m, 2H); 4.0–4.4 (m, 4H); 5.2 (d, 2H); 6.9 (d, 1H)

(xiv) 3,5,6-trifluoro-2-methoxy-4-methoxymethyl ($\pm$)-trans-3-(Z-2-chloro-3,3,3-trifluoroprop-1-en-1-yl)-2,2-dimethylcyclopropanecarboxylate (Product No 9).

90 MHz N.m.r (CDCl$_3$): (s, 3H); 1.34 (s, 3H); 1.75 (d, 1H); 2.4 (m, 1H); 3.41 (s, 3H); 3.95 (d, 3H); 4.57 (t, 3H); 5.23 (d, 2H); 6.1 (d, 1H)

(xv) 3,5,6-trifluoro-2-ethoxy-4-methoxymethylbenzyl ($\pm$)-cis-3-(Z-2-chloro-3,3,3-trifluoroprop-1-en-1-yl)-2,2-dimethylcyclopropanecarboxylate (Compond No 21).

100 MHz N.m.r (CDCl$_3$): 1.2–1.4 (m, 9H); 1.9–2.3 (m, 2H); 3.35 (s, 3H); 4.08 (q, 2H); 4.50 (t, 2H); 5.1 (d, 2H); 6.8 (d, 1H)

EXAMPLE 29

This Example illustrates the insecticidal properties of the Products of this invention.

The activity of the Product was determined using a variety of insect pests. The Product was used in the form of liquid preparations containing 500, 250 or 100 parts per million (ppm) by weight of the Product. The preparations were made by dissolving the Product in acetone and diluting the solutions with water containing 0.01% by weight of a wetting agent sold under the trade name "LISSAPOL" NX until the liquid preparations contained the required concentration of the Product. "Lissapol" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to three days after the treatment.

The results of the test are given in Table IV for each of the Products, at the rate in parts per million given in the second column as a grading of mortality designated as A, B or C wherein A indicates 80–100% mortality, B indicates 50–79% mortality and C indicates less than 50% mortality.

In Table IV the pest organism used is designated by a letter code and the pest species, the support medium or food, and the type duration of test is given in Table III.

TABLE III

| CODE LETTERS (Table IV) | TEST SPECIES | SUPPORT MEDIUM/FOOD | TYPE OF TEST | DURATION (days) |
| --- | --- | --- | --- | --- |
| TU | Tetranychus urticae | French bean | Contact | 3 |

TABLE III-continued

| CODE LETTERS (Table IV) | TEST SPECIES | SUPPORT MEDIUM/FOOD | TYPE OF TEST | DURATION (days) |
|---|---|---|---|---|
| | (spider mites - adult) | leaf | | |
| MP | *Myzus persicae* (aphids) | Chinese Cabbage leaf | Contact | 3 |
| NC | *Nephotettix cincticeps* (green leaf hopper - nymphs) | Rice plant | Contact | 3 |
| NL | *Nilaparvata lugens* (brown plant hopper - nymphs) | Rice Plant | Contact/ Residual | 6 |
| HV | *Heliothis virescens* (tobacco budworm - larvae) | Cotton leaf | Residual | 3 |
| DB | *Diabrotica balteata* (rootworm larvae) | Filter paper/ maize seed | Residual | 3 |
| BG | *Blattella germanica* (cockroach nymphs) | Plastic pot | Residual | 3 |
| MD | *Musca domestica* (houseflies - adults) | Cotton wool/ sugar | Contact | 1 |
| CP | *Chilo partellus* (stem borers larvae) | Oilseed rape | Residual | 3 |
| SP | *Spodoptera exigua* (lesser army worm - larvae) | Cotton leaf | Residual | 3 |

"Contact" test indicates that both pests and medium were treated and "residual" indicates that the medium was treated before infestation with the pests.

TABLE IV

| Compound No | Rate (ppm) | TU | MP | NL | NC | MD | BG | HV | DB | CP | SP |
|---|---|---|---|---|---|---|---|---|---|---|---|
| 1 | 500 | B | A | A | — | A | A | A | A | — | — |
| 2 | 500 | A | A | C | — | A | A | A | A | A | — |
| 3 | 500 | A | C | A | — | A | A | A | A | A | — |
| 4 | 500 | C | A | A | — | A | A | A | A | A | — |
| 5 | 500 | A | A | C | — | A | A | A | A | A | — |
| 6 | 500 | A | A | A | — | A | A | A | A | A | — |
| 8 | 500 | A | A | — | — | A | A | A | A | A | — |
| 9 | 500 | C | A | B | — | A | A | A | A | A | — |
| 10 | 500 | C | A | — | — | A | A | A | A | A | — |
| 11 | 500 | C | A | — | — | A | A | A | C | A | — |
| 12 | 100 | C | A | C | — | A | B | A | A | A | — |
| 13 | 100 | C | C | C | — | C | C | C | A | A | — |
| 14 | 500 | C | C | — | — | A | C | C | A | A | — |
| 15 | 100 | A | A | — | A | A | A | A | A | — | A |
| 20 | 100 | A | A | — | A | A | A | A | A | — | A |
| 21 | 500 | A | A | C | — | A | A | A | A | A | — |

EXAMPLE 30

This Example illustrates the knockdown properties of the compounds according to the invention.

1 cm$^3$ of a 125 ppm solution of the test chemical in acetone was sprayed into a Kearns and March chamber containing 20 *Musca domestica* (adult females).

Knockdown was observed over a period of 10 minutes and KT$_{90}$ values (the time taken for 90% of the insects to be knocked down) were calculated from the observations. Each test was replicated three times and mean KT$_{90}$ values were calculated. The results of these tests are given in Table V in the form of relative knockdown potency (RKP) compared with a standard chemical, tetramethrin, included in the test. The RKP values are calculated according to the formula:

$$RKP = \frac{\text{Mean } KT_{90} \text{ value of Tetramethrin}}{\text{Mean } KT_{90} \text{ value of Test Compound}}$$

TABLE V

| Compound No | RKP |
|---|---|
| 1 | 0.48 |
| 2 | 0.36 |
| 3 | 0.31 |
| 4 | 0.41 |
| 5 | 0.5 |
| 6 | 0.62 |
| 8 | 0.98 |
| 9 | 1.33 |
| 10 | 0.81 |
| 11 | 1.57 |
| 12 | 1.1 |
| 13 | 1.12 |
| 21 | 0.56 |

We claim:

1. A compound of formula

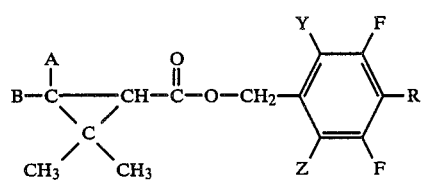

wherein Y represents alkoxy of up to six carbon atoms; Z represents halo or alkoxy of up to six carbon atoms; R represents a group of formula:

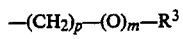

wherein each of m and p may have a value selected from zero and one, $R^3$ represents alkyl containing up to six carbon atoms, phenyl or benzyl, and additionally $R^3$ may represent alkenyl containing up to six carbon atoms, haloalkenyl containing up to six carbon atoms, alkynyl containing up to six carbon atoms or haloalkynyl containing up to six carbon atoms when m has the value zero; and either (a) A and B are both selected from alkyl containing up to four carbon atoms, or (b) A represents hydrogen and B represents a group of formula:

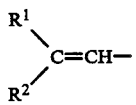

wherein $R^1$ and $R^2$ are each selected from methyl, fluoro, chloro, bromo and trifluoromethyl.

2. A compound according to claim 1 wherein R represents alkyl of up to four carbon atoms, alkoxy of up to four carbon atoms, alkenyl of up to four carbon atoms, alkynyl of up to four carbon atoms and alkoxymethyl of up to four carbon atoms in the alkoxy moiety.

3. A compound according to claim 1 wherein Y represents methoxy, Z represents fluoro, R is selected from methyl, methoxymethyl, allyl and propargyl, A represents hydrogen and B represents a group of formula:

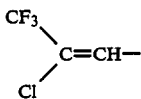

4. A compound according to claim 1 wherein A represents hydrogen and B represents a group of formula:

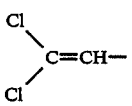

5. A compound according to claim 1 wherein both A and B represent methyl.

6. A compound according to claim 1 selected from the group of compounds consisting of
2,4-dimethoxy-3,5,6-trifluorobenzyl (±)-cis-3-(Z-2-chloro-3,3,3-trifluoroprop-1-en-1-yl)-2,2,-dimethyl-cyclopropanecarboxylate,
3,5-difluoro-2,6-dimethoxy-4-methylbenzyl (±)-cis-3-(Z-2-chloro-3,3,3-trifluoroprop-1-en-1-yl)-2,2-dimethyl-cyclopropanecarboxylate,
3,5-difluoro-2,4,6-trimethoxybenzyl (35 )-cis-3-(Z-2-chloro-3,3,3-trifluoroprop-1-en-1-yl)-2,2-dimethylcyclopropanecarboxylate,
4-methyl-2-methoxy-3,5,6-trifluorobenzyl (±)-cis-3-(Z-2-chloro-3,3,3-trifluoroprop-1-en-1-yl)-2,2-dimethyl-cyclopropanecarboxylate,
2-methoxy-4-methoxymethyl-3,5,6-trifluorobenzyl (±)-cis-3-(Z-2-chloro-3,3,3-trifluoroprop-1-en-1-yl)-2,2-dimethylcyclopropanecarboxylate,
4-allyl-2-methoxy-3,5,6-trifluorobenzyl (±)-cis-3-(Z-2-chloro-3,3,3-trifluoroprop-1-en-1-yl)-2,2-dimethylcyclopropanecarboxylate,
2-methoxy-4-methoxymethyl-3,5,6-trifluorobenzyl (±)-trans-3-(Z-2-chloro-3,3,3-trifluoroprop-1-en-1-yl)-2,2-dimethylcyclopropanecarboxylate,
2-methoxy-4-methoxymethyl-3,5,6-trifluorobenzyl (±)-cis-3-(2,2-dichloroethenyl)-2,2-dimethylcyclopropanecarboxylate,
2-methoxy-4-methoxymethyl-3,5,6-trifluorobenzyl (±)-trans-3-(2,2-dichloroethenyl)-2,2-dimethylcyclopropanecarboxylate and,
2-methoxy-4-methoxymethyl-3,5,6-trifluorobenzyl 2,2,3,3-tetramethylcyclopropanecarboxylate.

7. A process for preparing a compound according to claim 1 wherein either:

(a) an acid of formula (II)

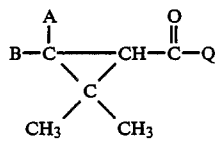

wherein Q represents the hydroxy group and A and B have any of the meanings given in claim 1, is reacted with an alcohol of formula (III)

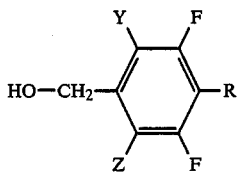

wherein Y, Z and R have any of the meanings given in claim 1, the reaction taking place in the presence of an acid catalyst or a dehydrating agent; or (b) an acid halide of formula

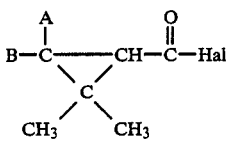

wherein A and B have any of the meanings given in claim 1 and Hal represents a halogen atom, is reacted with an alcohol of formula (III) wherein Y, Z and R have any of the meanings given in claim 1, the reaction taking place in the presence of a base; or (c) an acid of formula (II) wherein Q represents the hydroxy group and A and B have any of the meanings given in claim 1 is reacted with a halide of formula (IV):

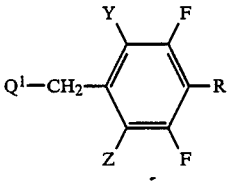

wherein $Q^1$ represents a halogen atom and Y, Z and R have any of the meanings given in claim 1, or with the quaternary ammonium salts derived from such halides by reaction with tertiary amines; or (d) a lower alkyl ester of formula

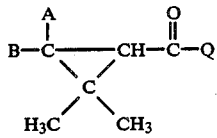

wherein Q represents a lower akoxy group containing up to six carbon atoms and A and B have any of the meanings given in claim 1, is heated with an alcohol of formula (III) to effect a transesterification reaction.

8. A compound of formula:

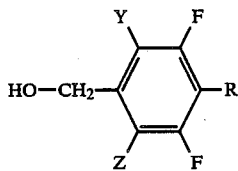

wherein Y, R and Z have any of the meanings given in claim 1.

9. A compound according to claim 8 of formula:

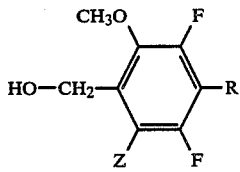

wherein Z is selected from fluoro and methoxy and R is selected from methyl, methoxymethyl, allyl and propargyl.

10. A compound of formula:

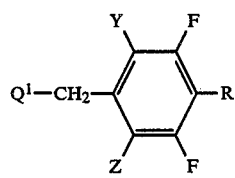

wherein $Q^1$ represents a halogen atom and Y, Z and R have any of the meanings given in claim 1.

11. An insecticidal composition comprising an insecticidally effective amount of a compound according to claim 1 in association with an insecticidally inert carrier or diluent.

12. A composition according to claim 11 in the form of granules of inert carrier coated or impregnated with a compound according to claim 1.

13. A composition according to claim 11 adapted for application by aerosol.

14. A method of combating insect pests at a locus in which an insecticidally effective amount of a composition according to claim 11 is applied to the locus.

* * * * *